United States Patent [19]

Ciarlei

[11] Patent Number: 4,996,974
[45] Date of Patent: Mar. 5, 1991

[54] ADJUSTABLE STEERING CONTROL FOR FLEXIBLE PROBE

[75] Inventor: Joseph A. Ciarlei, Marcellus, N.Y.

[73] Assignee: Welch Allyn, Inc., Skaneateles Falls, N.Y.

[21] Appl. No.: 338,940

[22] Filed: Apr. 17, 1989

[51] Int. Cl.[5] .............................................. A61B 1/00
[52] U.S. Cl. ........................................ 128/4; 138/120
[58] Field of Search ............................. 128/4; 138/120

[56] References Cited

U.S. PATENT DOCUMENTS

| | | | |
|---|---|---|---|
| 4,700,693 | 10/1987 | Lia et al. ................................. | 128/4 |
| 4,762,118 | 1/1988 | Lia et al. ................................. | 128/4 |
| 4,762,119 | 9/1988 | Allred, III et al. ..................... | 128/4 |
| 4,787,369 | 10/1988 | Allred, III et al. ..................... | 128/4 |
| 4,790,294 | 12/1988 | Allred, III et al. ..................... | 128/4 |
| 4,841,950 | 6/1989 | Fukuda ................................... | 128/4 |

Primary Examiner—William H. Grieb
Attorney, Agent, or Firm—Wall and Roehrig

[57] ABSTRACT

A control unit for a steerable probe of the type having a flexible insertion tube and a distal steering section which is articulated by displacing a pair of steering cables has a pair of pulleys which can be displaced within the housing to take up slack on the cables. A carrier plate for threaded sheath adjusters for the cable sheaths has a pair of threaded bores for the adjusters and a second pair of threaded bores that extend from the periphery of the carrier plate into the first bores. A pair of threaded set screws lock the adjusters at locking positions relative to the carrier plate. A plurality of set screws are distributed about the circumference of the distal end of the control housing. These set screws releasable engage the proximal portion of a strain relief fitting. This permits the strain relief fitting and the associated insertion tube to be rotated to a desired position relative to the housing. Then the strain relief fitting can be locked to the housing at the desired position, with the insertion tube bending access aligned with the access of the control housing.

11 Claims, 4 Drawing Sheets

ADJUSTABLE STEERING CONTROL FOR FLEXIBLE PROBE

BACKGROUND OF THE INVENTION

This invention relates to a controllably bendable tube assembly, especially a borescope or endoscope of the type having a cable-actuated hollow steering section.

A borescope is generally characterized as an elongated flexible insertion tube with a viewing head at its distal or forward end, and a control section at its proximal end for controlling the bending at the distal end. In such a borescope, a bendable tube steering section is situated at the distal end adjacent to the viewing head. One or two pairs of control cables extend through the bendable tube section and the remainder of the insertion tube and connect with a steering control mechanism in the control section. One or both pairs of these cables are differentially displaced for bending the steering section to facilitate the inspection of a remote object.

A borescope is typically intended for visual inspection of an intricate mechanical assembly, such as a jet engine or turbine, where it would be difficult or impossible otherwise to view the assembly's internal elements. The borescope needs to be insertable into narrow, tortuous passageways, and must observe very delicate steering considerations.

It is necessary that cable slack be minimized to avoid slack or play in steering. Also, the compression load applied to the cable sheaths must be accurately maintained. Furthermore, the steering horizon for the control section should be aligned as closely as possible with the bending axis of the steering section, despite the cumulative alignment errors that may occur in assembly of the borescope.

An endoscope is typically inserted into a body cavity of a patient for visual inspection of tissues within the cavity. Because body passages such as esophagus, bronchia, and colon are narrow and tortuous, the steering section must be bent rather precisely, and as close to the viewing head as possible. Thus, cable tension must be limited and cable slack minimized as much as possible.

The opposing steering cables of each pair are required to displace to deflect the distal tip. The cables are differentially displaced, that is, as one cable is drawn into the control section, the other is released a like amount. However, the motion of one cable is not the exact opposite of the motion of the other. Also, coiling of the insertion tube can result in tensioning of both cables at the same time. For these and other reasons, there is a tendency for cables to stretch over time, leading to slop or play in steering, with ensuing loss of precision.

Moreover, it is difficult or impossible to maintain accurate adjustment of cable sheath forces during assembly. The usual, conventional installation of cable sheaths involves adjusting a threaded cable adjuster in a threaded bore in a carrier within the housing of the control section. There are lock nuts on the threads of the cable adjusters, and the lock nuts are tightened against the carrier to keep the adjuster in place. However, tightening of the lock nut frequently results in rotations of the cable sheath adjuster, and this results in loosening or overstressing the cable sheath.

Moreover, it is desirable to keep the axis of bending of the steering section aligned as closely as possible with the axis of the steering control mechanism of the control section. However, in conventional borescopes, some errors in alignment do exist within the control section, and these can accumulate over the numerous steps of assembly. Once the conventional probe device is assembled, it is difficult or impossible to adjust the tube orientation relative to the control section.

OBJECT AND SUMMARY OF THE INVENTION

Accordingly, it is an object of this invention to provide a borescope, endoscope, or similar flexible, steerable probe which avoids the drawbacks of the prior art.

It is another object of this invention to provide a cable bendable probe in which cable tension can be adjusted so as to take up slack which may develop over prolonged use.

It is still another object of this invention to provide a cable steerable probe whose bending axis can be simply and easily aligned and locked relative to a corresponding steering axis of its control housing.

It is yet another object of this invention to provide a cable steerable probe whose cable sheaths can be accurately adjusted for position and securely locked relative to the control housing.

In accordance with an aspect of this invention, an adjustable steering control mechanism is provided for a borescope, endoscope, or similar probe of the type that has an elongated flexible insertion tube, a distal steering section, and at least one pair of steering cables for controlling the bending of the steering section. The steering cables are enclosed in respective cable sheaths. A control housing is disposed at a proximal end of the insertion tube and includes a rotatable shaft or equivalent means for displacing the control cables relative to the sheaths. An adjustable steering control mechanism includes a pair of pulleys in the housing over which the steering cables pass between the ends of the sheaths and the displacing means. Means are provided in the housing for adjusting the position of the pulleys to take up slack in the cables.

In a preferred embodiment, the pulleys are mounted on a carrier plate that is slidably positioned on a longitudinal frame within the housing. An adjuster tube in the housing can be rotated after removing a threaded end cap on the housing. The adjuster tube has threads which mate with threads on the pulley carrier plate, so that rotation of the adjuster tube results in linear movement of the pulley carrier plate.

Another important feature of this invention is that the bending axis of the insertion tube steering section can be adjusted to match the axis of steering of the control housing. Here, the proximal end of the insertion tube is seated in a strain relief fitting which has a proximal portion that fits into a distal end of the control housing. There are a plurality of set screws distributed about the circumference of the housing releasably engaging the proximal portion of the strain relief fitting. This permits the strain relief fitting and the insertion tube to be rotated to a desired position relative to the housing, and then locked by tightening the set screws with the strain relief fitting being held at its desired orientation relative to the housing. Preferably the proximal portion of the strain relief fitting has an annular groove on its radially outward face that engages the housing, and the set screws are received into this annular groove.

Another important feature of this invention is that the sheath adjusters can be accurately positioned and locked in place. A pair of threaded sheath adjusters abut respective proximal ends of the cable sheaths. A carrier plate for the cable sheath adjusters, located within the housing, has a pair of threaded bores through it and the adjusters are threadably secured into these bores. Another pair of bores extend respectively into the first-mentioned bores from the periphery of the carrier plate. A pair of set screws in the second pair of bores turn down to lock the sheath adjusters at the desired positions relative to the carrier plate. A tubular casing for the control housing can have a mounting hole in its tubular wall at a position that corresponds to one of the second pair of threaded bores in the sheath adjuster carrier plate. The tubular casing can be secured to the carrier plate by a threaded fastener that passes through the mounting hole into the threaded bore above the set screw.

The above and other objects, features, and advantages of this invention will become apparent to persons skilled in this art from the ensuing description of a preferred embodiment, which should be read in conjunction with the accompanying Drawing.

DETAILED DESCRIPTION OF THE PREFERRED EMBODIMENT

Figure 1:
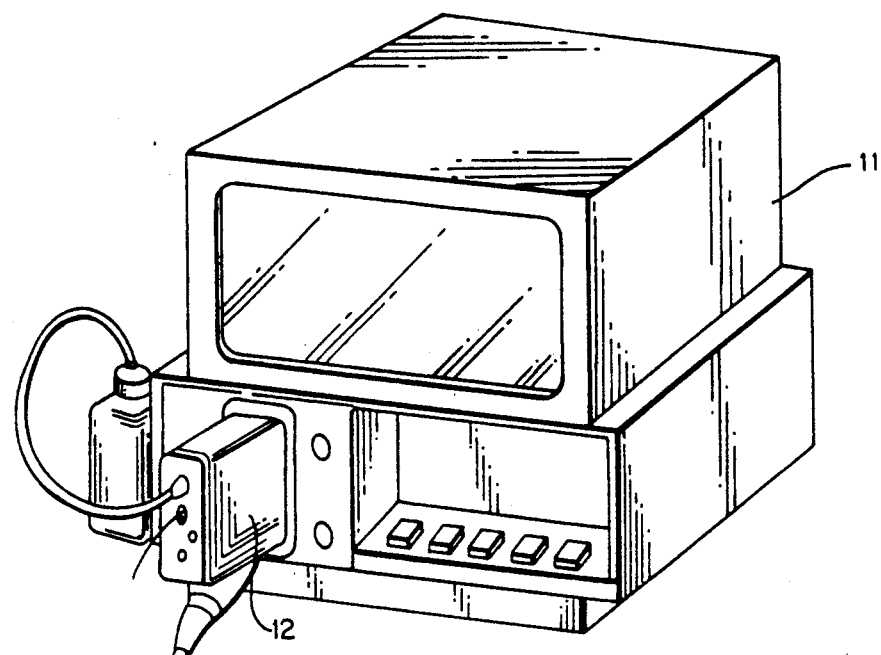
FIG. 1 is a perspective view of a video borescope of the cable-steerable type, which employs a steering control assembly according to the present invention.
Figure 1:
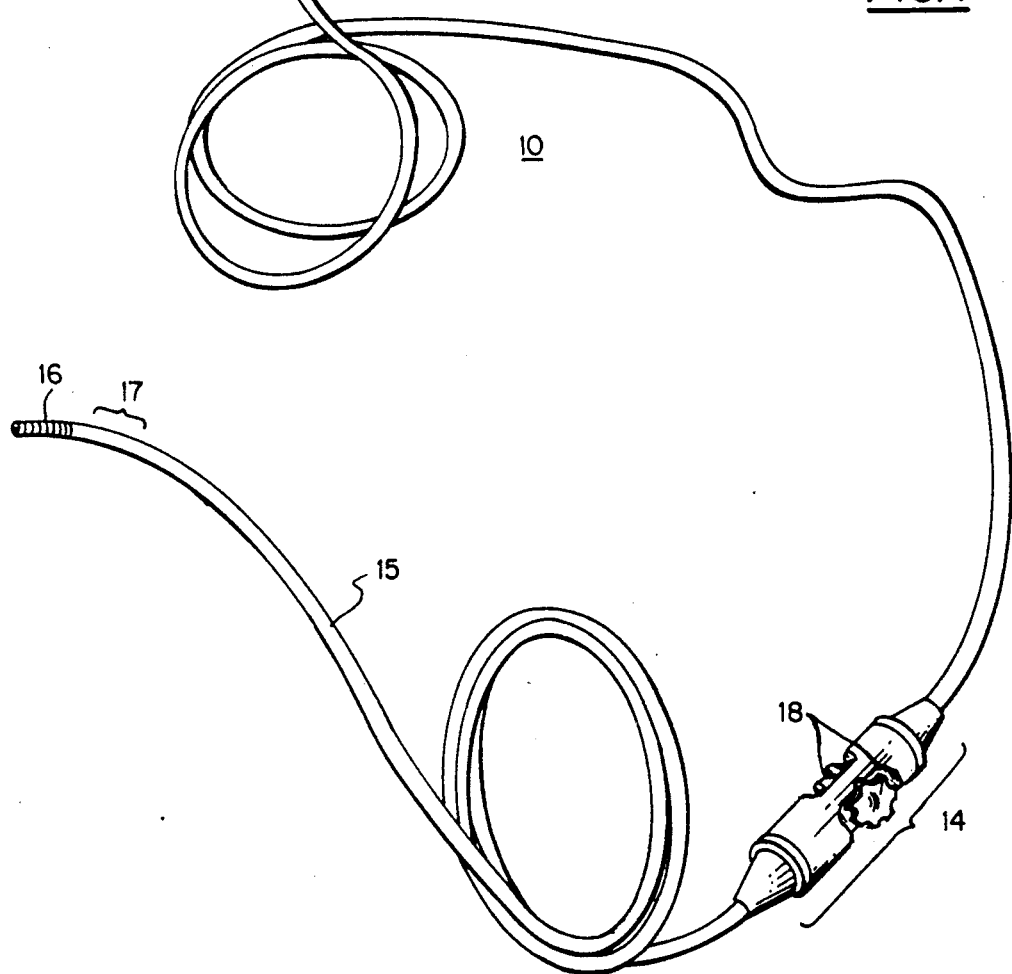

With reference to the Drawing, FIG. 1 shows a video borescope system 10 having a video monitor and console 11, with a connector adapter 12 that connects the console 11 to an umbilical or power tube 13 leading to a borescope steering control unit 14. An elongated flexible insertion tube 15 extends distally from the control unit 14, and has a video probe head 16 at its tip with a bending or steering section 17 connecting the flexible insertion tube 15 to the head 16. Knobs 18,18 on the control unit 14 rotate to control articulation up and down of the bending section 17, by means of steering cables within the sheath of the insertion tube 15.

Figure 2:
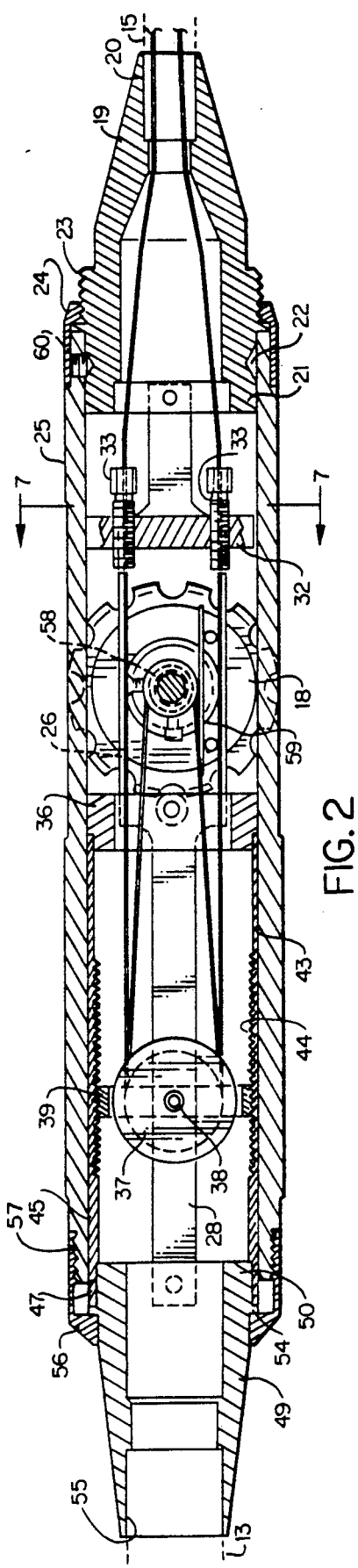
FIGS. 2 and 3 are side elevation and top plan sectional views, respectively, of the control assembly of a preferred embodiment of this invention.
Figure 3:
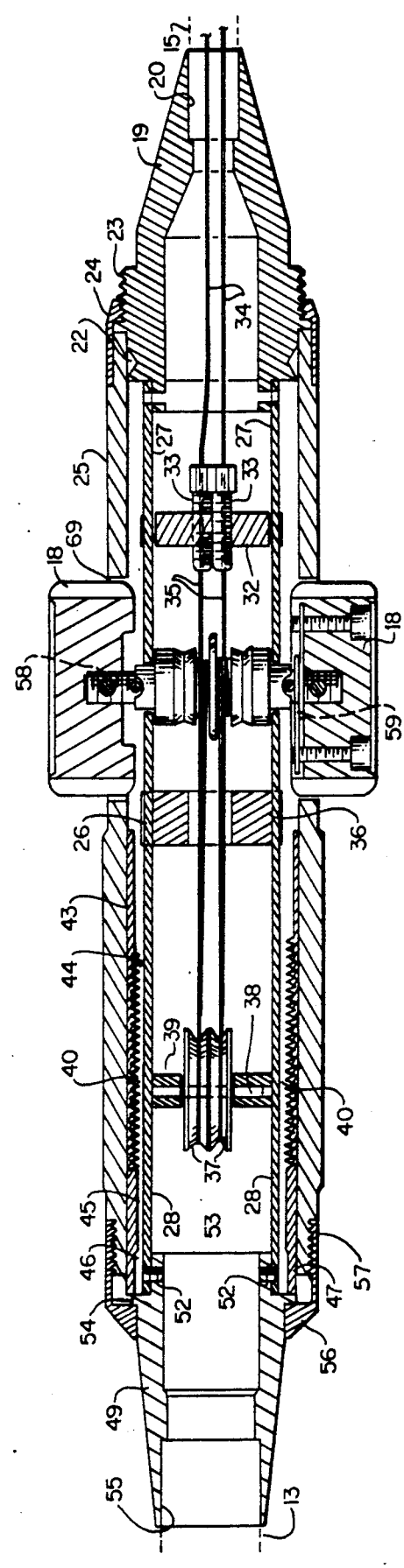

With reference additionally to FIG. 2 and 3, the control unit 14 has a strain relief fitting 19 of generally conical shape at the distal end of the control unit 14. A distal socket 20 in the fitting 19 receives the insertion tube 15. A proximal portion 21 of the strain relief fitting 19 is generally cylindrical and has an annular V-groove 22 in its cylindrical face. A male thread 23 on the fitting 19 receives a threaded cap nut 24.

Figure 4:
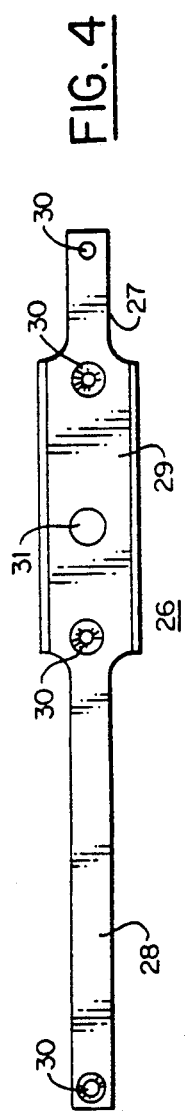
FIG. 4 shows an arm constituting a longitudinal frame member of the control housing of the preferred embodiment.

The control unit has a tubular housing outer sleeve 25, a distal end of which receives the strain relief fitting 19. The nut 24 has a cylindrical flange to cover the distal end of the sleeve 25. A pair of arms 26, one of which shown more specifically in FIG. 4, each have an elongated distal member 27, an elongated proximal member 28, and a widened middle portion 29. Through-holes 30 are provided at ends of the members 27 and 28, and near the ends of the middle portion 29, for receiving threaded fasteners. A round opening 31 is provided in the middle portion 29 to receive a steering shaft to be described latter.

A generally round cap or plate 32 serves as a mount for threaded cable sheath adjusters 33, a pair of which abut the proximal ends of cable sheaths 34 for a corresponding pair of steering cables 35.

Another generally round cap or plate 36 having an open center joins the two arms 26 at a proximal end of the middle portion 29 thereof.

Figure 5:
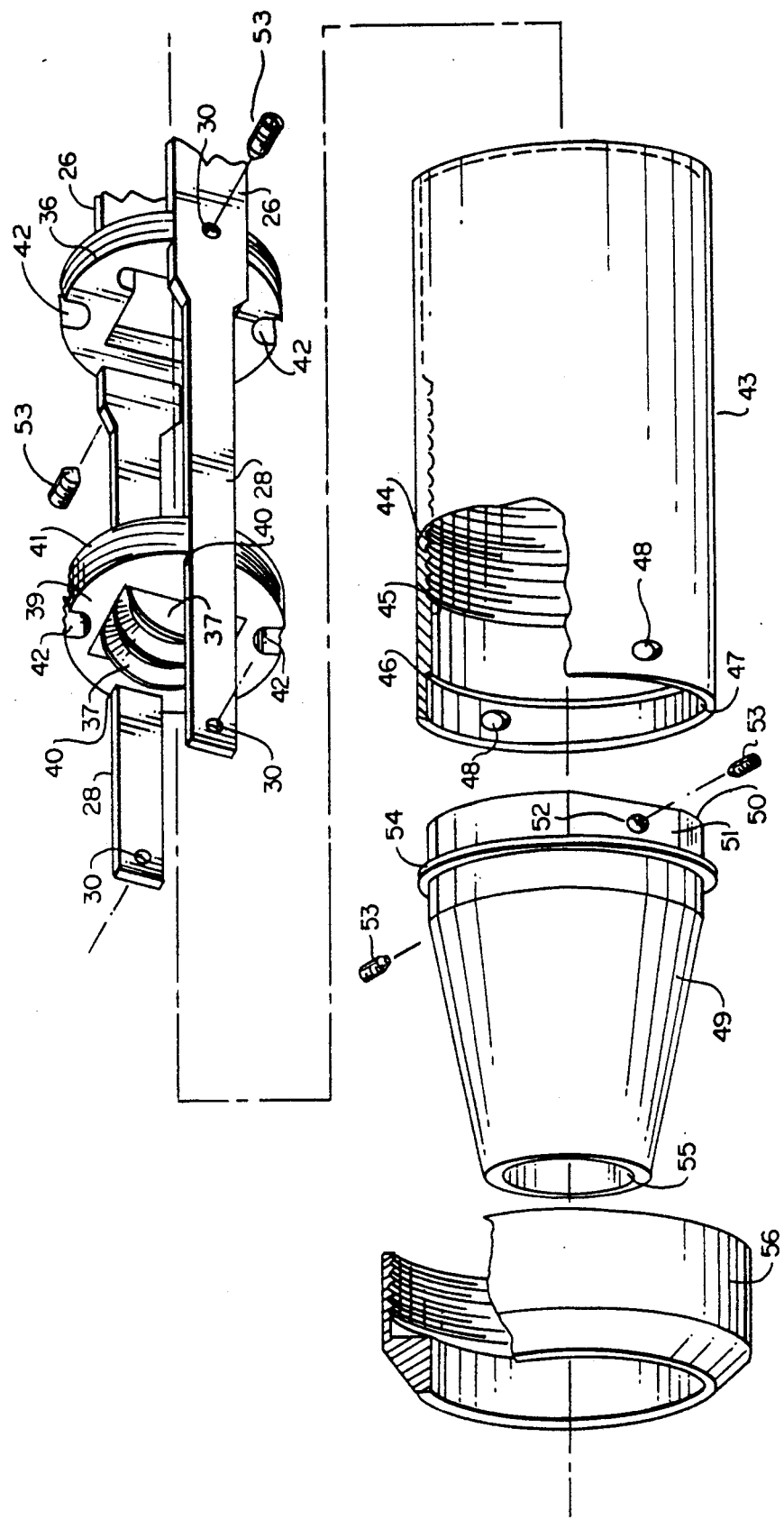
FIG. 5 is an exploded assembly view of a proximal portion of the preferred embodiment.

A pair of pulleys 37 are mounted on a pivot pin 38 that is held on a pulley cap or carrier plate 39. Lateral cutouts 40 at opposite sides of the plate 39 permits slidable mounting of the cap or plate 39 on the arm proximal members 28. As shown in FIG. 5, the pulley cap or carrier plate 39 has a male helical thread 41 on its periphery and has peripheral cutouts 42 for passing the fiber optic bundle and electrical cables of the borescope.

An adjuster tube or sleeve 43 fits over the proximal arm members 28 and the pulley cap 39. Internal female threads 44 within the sleeve 43 engage the thread 41 of the cap or plate 39. A reduced-diameter wall 45 near the proximal end of the tube 43 defines a limit to the travel of the pulley cap 39. The reduced-diameter wall ends at a shoulder 46, and a cylindrical end flange 47 extends proximally from the shoulder 46. A pair of openings 48 are provided at opposite positions in this end flange 47.

A proximal stain relief fitting 49 has a distal end 50 with flat side wall 51 and threaded openings 52 therein. Threaded fasteners 53 are inserted through the through holes 30 at the proximal end of the arms 26 into these openings 52 to hold the fitting 49 after the adjuster tube 43 is installed. The openings 48 permit access to these screw fasteners 53.

An annular flange 54 of the fitting 49 extends radially over the adjuster tube cylindrical flange 47. The fitting 49 has a proximal end socket 55 into which the power tube or umbilical 13 is fitted.

A threaded cap nut 56 is installed in place over the strain relief fitting 49. This cap nut has threads that engage threads at the proximal ends of the housing outer sleeve 45. The cap nut 56 has a cylindrical flange to cover the proximal part of the adjuster tube or sleeve 43. The cap nut 56 can be turned to remove it and expose the end of the adjuster tube.

A steering shaft 58 extends between the knobs 18, 18 and through the opening 31 in the arms 26. The steering cables extend from the tip of the insertion tube 15 back through the cable adjusters 33, over the pulleys 37, and back to the shaft 58 where they are attached. A spring 59 on the shaft 58 can be included to provide a return-to-zero feature.

Figure 6:
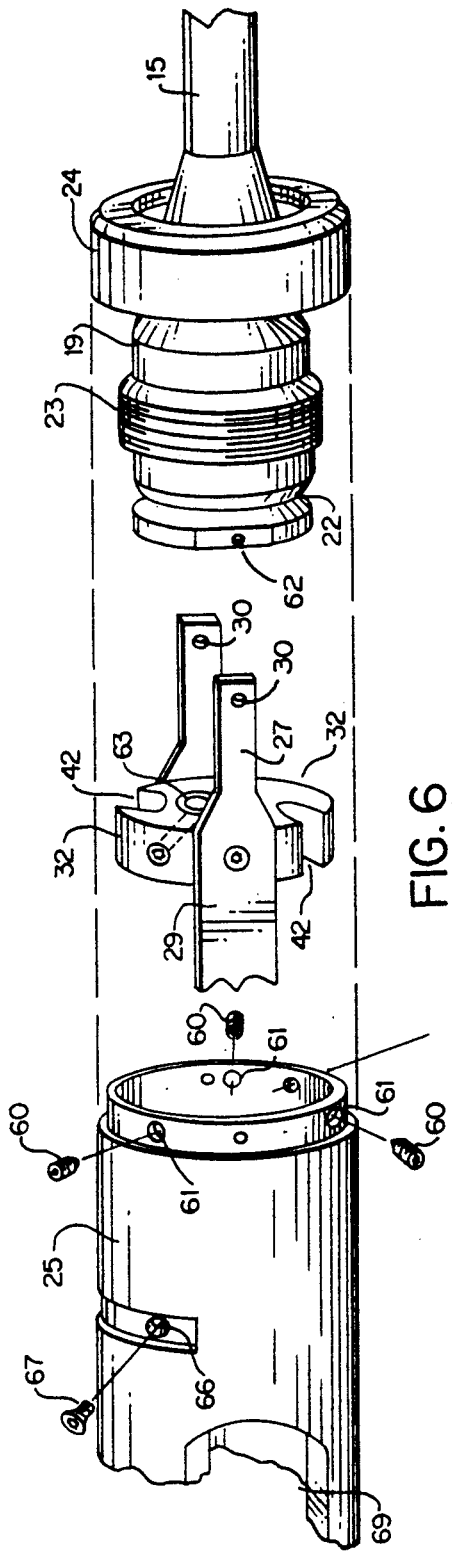
FIG. 6 is an exploded assembly view of a distal portion of the preferred embodiment.
Figure 7:
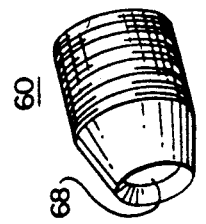
FIG. 7 is a sectional view taken at line 7—7 of FIG. 2.
Figure 8:
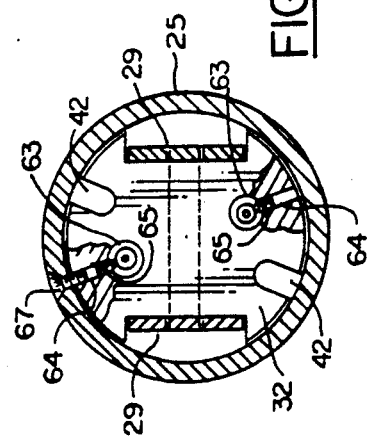
FIG. 8 is an enlarged view of a set screw employed in the preferred embodiment.

As shown in FIGS. 6, 7, and 8 three set screws 60 enter into threaded openings 61 at the distal end of the housing outer sleeve 25, and engage the V-groove 22 of the distal strain relief fitting.

During initial installation and construction, a removable pin is inserted through the through holes 30 at the distal ends of the arm distal members 27 and through a bore 62 in the strain relief fitting 19.

When assembly is substantially complete and the housing outer sleeve 25 is slid forward over the arms, this pin is removed, and the set screws 60 are turned down so the tips or noses thereof engage in the annular V-groove 22. The strain relief fitting 19 together with the insertion tube 50 can be rotated slightly until the bending axis of the bending or steering section 17 is properly aligned with the axis of the steering shaft 58. Then, the set screws 60 can be tightened down to lock the strain relief fitting 19 against further rotation.

As shown in FIGS. 6 and 7, the cable sheath adjuster cap 32 has longitudinal or axially bores 63 through it which are threaded for receiving the cable sheath adjusters 33. An additional pair of bores 64 extend at right angles into the axial bores 63 from the periphery of the cap 32. A respective pair of set screws 65 which can be identical to the set screws 60 engage threads within the bores 64, and are turned down against the adjusters 33 to lock them against rotation.

A through hole 66 is provided in the tubular wall of the housing outer sleeve 25 at the location of one of the bores 64 in the adjuster cap 32. A machine screw 67 which has the same thread as the set screw 65 and the bore 64, extends through the hole 66 into the bore 64 and secures the housing outer sleeve 25 securely to the frame that is formed by the arms 26 the cap 32 and the cap 36.

As shown in FIG. 8, the set screws 60 preferably have a cup-shaped or concave point 68. Thus, with this type of set screw, the metal or other material of the V-groove 22 or of the adjusters 33 will tend to flow upwards under pressure into the cup 68 to form a land and provide an extremely secure and sure grip.

As also shown in FIG. 6, cutouts 69 are provided at the sides of the tubular outer sleeve 25 to accommodate the knobs 18.

Various cable-operated articulation sections are known, for example those disclosed in U.S. Pat. Nos. 4,700,693 and 4,790,294.

While this invention has been described in detail with reference to a single preferred embodiment, it should be understood that the invention is not limited to that precise embodiment. Rather, many modifications and variations will present themselves to those skilled in the art without departing from the scope and spirit of this invention, as defined in the appended claims.

What is claimed is

1. An adjustable steering control assembly for a steerable probe of the type having an elongated flexible insertion tube, a distal steering section, at least one pair of steering cables that are enclosed in respective cable sheaths for controlling the bending of said steering section, a control housing disposed at a proximal end of said insertion tube, and means in said control housing for displacing said control cables relative to said sheaths; said adjustable steering control mechanism including a pair of pulleys in said housing over which said cables pass between ends of said sheaths and said displacing means, and means for selectively adjusting the positions of said pulleys within said housing to reduce slack on said cables.

2. An adjustable steering control assembly according to claim 1, further comprising a longitudinal frame in said housing, a pulley carrier slidably positioned on said frame, and on which said pulleys are pivotally mounted, and means for adjusting the longitudinal position of said pulley carrier on said frame.

3. An adjustable steering control assembly according to claim 2, wherein said pulley carrier has a helical thread on its periphery, and said adjusting means includes a rotatable adjusting tube having an internal thread engaging the thread of the pulley carrier, such that the longitudinal position of the pulley carrier is adjusted by rotating the adjusting tube.

4. An adjusting steering control assembly according to claim 3, wherein said control mechanism further includes a strain relief member mounted at a proximal end of said frame and including an engaging flange for retaining said adjusting tube.

5. An adjustable steering control assembly according to claim 4, comprising a casing disposed over said frame and said adjusting tube, and a proximal sleeved nut removably fitting over said casing and said strain relief member, said casing terminating in advance of a proximal end of said adjusting tube, such that a portion of said tube is exposed when said proximal sleeved nut is removed.

6. A steering control mechanism for a steerable probe of the type having an elongated flexible insertion tube, a distal steering section, at least one pair of steering cables that are enclosed in respective cable sheaths for controlling the bending of said steering section, a control housing disposed at a proximal end of said insertion tube, means in said control housing for displacing said control cables relative to said sheaths, a pair of threaded sheath adjusters abutting the respective proximal ends of said cable sheaths, a carrier plate for said adjusters having a first pair of bores therethrough into which said threaded adjusters are mounted and a second pair of threaded bores extending from the periphery of said carrier plate into said first bores, and a respective pair of threaded set screws in said second bores for locking said adjusters at selected positions relative to said carrier plate.

7. A steering control mechanism according to claim 6 further comprising a tubular casing for said steering control mechanism and having a mounting hole through a tubular wall thereof at a position that corresponds to one of said second threaded bores in said carrier plate, and a threaded fastener connecting said tubular casing to said carrier plate through said mounting hole and into said one of said second threaded bores.

8. A steering control mechanism for a steerable probe or the type having an elongated flexible insertion tube, a distal steering section that bends in a predetermined plane, at least one pair of steering cables that are enclosed in respective cable sheaths for controlling the bending of said steering sections, a control housing disposed at a proximal end of said insertion tube, a control shaft that is rotatable in a predetermined plane relative to the housing to displace said cables relative to said sheaths, a strain relief fitting having a distal portion into which the proximal end of said insertion tube is affixed and a proximal portion which fits into a distal portion of said control housing, a plurality of set screws means distributed about the circumference of the distal end of said control housing for releasably engaging the proximal portion of said strain relief fitting, permitting the strain relief fitting and the insertion tube to be rotated to a desired position relative to said housing and then locking the strain relief fitting to the housing at said desired position.

9. The steering control mechanism of claim 8 said proximal portion of the strain relief fitting having an annular groove on a face thereof that engages said housing distal end to receive said set screw means.

10. The steering control mechanism according to claim 8 further comprising a sleeved nut having a female threaded distal portion engaging a thread on said strain relief fitting.

11. The steering control mechanism according to claim 8, wherein said set screw means included set screws which have hollow cup-shaped engaging noses.

* * * * *